United States Patent
Steinberger et al.

(10) Patent No.: US 6,719,921 B2
(45) Date of Patent: Apr. 13, 2004

(54) PROCESS FOR THE CONTINUOUS PRODUCTION OF MIXTURES OF SUBSTANCES AND REACTION MIXTURES AND DEVICE FOR ITS IMPLEMENTATION

(75) Inventors: Michael Steinberger, Velden (AT); Josef Miklautsch, Villach (AT)

(73) Assignee: Degussa AG, Düsseldorf (DE)

( * ) Notice: Subject to any disclaimer, the term of this patent is extended or adjusted under 35 U.S.C. 154(b) by 97 days.

(21) Appl. No.: 09/963,660

(22) Filed: Sep. 27, 2001

(65) Prior Publication Data

US 2002/0044494 A1 Apr. 18, 2002

(30) Foreign Application Priority Data

Sep. 29, 2000 (DE) .......................... 100 48 513

(51) Int. Cl.⁷ .......................... C09K 3/00; C07C 409/24
(52) U.S. Cl. ...................................... 252/186.42; 562/6
(58) Field of Search .................. 562/6; 252/186.42; 137/9; 366/152.1, 152.2, 160.2, 336, 136, 137

(56) References Cited

U.S. PATENT DOCUMENTS

| | | | | |
|---|---|---|---|---|
| 3,266,780 A | * | 8/1966 | Waters | 366/152.1 |
| 3,425,668 A | * | 2/1969 | Koeng et al. | 366/152.2 |
| 3,817,658 A | | 6/1974 | Murase | 417/2 |
| 4,019,653 A | | 4/1977 | Scherer et al. | 222/1 |
| 4,176,672 A | | 12/1979 | Borberg | 137/99 |
| 4,399,105 A | * | 8/1983 | Tilgner et al. | 366/152.1 |
| 4,433,701 A | * | 2/1984 | Cox et al. | 366/152.2 |
| 4,440,314 A | | 4/1984 | Vetter et al. | 222/39 |
| 4,614,438 A | * | 9/1986 | Kobayashi | 366/152.1 |
| 4,621,927 A | * | 11/1986 | Hiroi | 366/132 |
| 4,642,222 A | * | 2/1987 | Brazelton | 366/152.2 |
| 4,964,732 A | * | 10/1990 | Cadeo et al. | 366/152.1 |
| 5,332,311 A | * | 7/1994 | Volk et al. | 366/152.2 |
| 5,423,607 A | * | 6/1995 | Jones et al. | 366/152.2 |
| 5,482,368 A | * | 1/1996 | Nakamura et al. | 366/152.2 |
| 5,676,461 A | * | 10/1997 | Edwards | 366/152.2 |
| 5,823,669 A | * | 10/1998 | Jones | 366/152.1 |
| 5,887,975 A | | 3/1999 | Mordaunt et al. | 366/152.1 |

FOREIGN PATENT DOCUMENTS

| | | |
|---|---|---|
| DE | 3638552 | 5/1988 |
| DE | 3800788 | 7/1989 |
| EP | 0026874 | 4/1981 |
| EP | 0641777 | 3/1995 |

* cited by examiner

*Primary Examiner*—Tony G. Soohoo
(74) *Attorney, Agent, or Firm*—Smith, Gambrell & Russell

(57) ABSTRACT

A process for the continuous production of a mixture of substances or of a reaction mixture that has been formed by reaction of components contained therein. The component streams withdrawn from a storage container (1, 2 or 3) or a distribution network (12) are each conveyed via a controlled system (22, 23, 24, 25) which in each instance comprises a flow-measuring device (8, 9, 10, 11) and a regulating element (34, 35, 36, 37). The flow-rates of the individual components are regulated in quantitatively proportional manner with reference to the flow-rate of a first component. The resulting regulated flow-rates are introduced into a receiving container, either directly or after individual flow-rates have been completely or partially conducted together. The process and the device are especially suitable for the on-site production of mixtures of substances that cannot be transported or that can only be transported in elaborate manner, such as relatively highly concentrated solutions of peroxycarboxylic acid.

21 Claims, 2 Drawing Sheets

PROCESS FOR THE CONTINUOUS PRODUCTION OF MIXTURES OF SUBSTANCES AND REACTION MIXTURES AND DEVICE FOR ITS IMPLEMENTATION

INTRODUCTION AND BACKGROUND

The present invention is directed towards a process for the continuous production of a mixture of substances or of a reaction mixture that has been formed therefrom by being allowed to stand, comprising bringing together the individual components forming the mixture of substances in quantitatively proportional ratio and, in the case of the production of a reaction mixture, allowing the mixture of substances to stand in a vessel until the desired conversion has been established, in particular until the establishment of the state of equilibrium of components forming an equilibrium composition.

In another aspect, the present invention relates to a device for implementing the process, said device being capable of being set up as an on-site plant and being especially suitable for the production of solutions of peroxycarboxylic acid.

As a rule, chemical reactions have been carried out hitherto in reactors of highly variable design. The reaction components are supplied to the reactor either in succession or simultaneously and are mixed and converted therein. After thorough mixing has taken place and after the reaction has flattened out, the product is dispensed into shipping containers or storage containers, provided that no special processing ensues. Significant disadvantages of this process are the high investment costs, since on the one hand reactors which in certain cases have been specially constructed with appropriate capacity are required and, in addition, in many cases, for example in the case of the use and/or formation of products with high oxidation potential and also of readily combustible and/or explosive substances or mixtures of substances, out of safety considerations a considerable effort has to be made in respect of safety appliances and the control thereof. Further disadvantages of the conventional devices are the long feed-times and also the high effort in respect of cleaning the entire plant in the case of a change of product.

From U.S. Pat. No. 5,887,975 a multiple-component in-line paint-mixing system is known in which the individual components of the paint are not mixed and homogenized in a mixing container but in which the individual components are conveyed in pulsed manner and in succession in quantitatively proportional ratio through a reducing manifold and the individual components flowing in succession in pulsed segments in the discharge line are conducted together in an integrator immediately prior to spraying of the paint and are mixed in a static mixer. By virtue of this arrangement it is also possible to meter and to mix components that are capable of reacting with one another, in such a way that the actual reaction takes place only after the paint has been sprayed.

The previously appraised process is less suitable for the production of mixtures of substances and reaction mixtures that can finally be stored in a container, because the pulsed metering results in long feed-times. In addition, from the point of view of safety the process cannot be used when certain combinations of the components forming the mixture are themselves explosive. As a result of the transportation of the components in succession through the same line, such problems are unavoidable.

In the course of the production of equilibrium peroxycarboxylic acids, for example, it is of essential importance to meter the individual components in the correct order, since otherwise explosive mixtures may arise. In the case of the equilibrium peroxycarboxylic acids, care has to be taken to ensure that highly concentrated aqueous hydrogen peroxide is brought into contact as the final component with a mixture consisting of a carboxylic acid, water and a mineral-acid catalyst.

An object of the invention is accordingly to enable a process with which mixtures of substances that contain components capable of reacting with one another, accompanied by release of moderate heat of reaction, can be produced continuously, whereby the actual reaction only takes place in the shipping container or in an intermediate container that has been provided for further use.

According to a further object, the process should be capable of being regulated reliably. Ultimately, the process should be capable of being used for the safe production of aqueous solutions of peroxycarboxylic acid.

According to a further object of the invention, a device for implementing the process should be made available. The device should be of simple construction and capable of being set up as an on-site plant directly by the users of the mixture of substances or of the reaction mixture, in order in this way to avoid the transportation of, in certain cases, critical mixtures of substances such as equilibrium peroxycarboxylic acids of relatively high concentration.

SUMMARY OF THE INVENTION

These and further objects such as are apparent from the further description can be achieved by the process according to the invention. A process for the continuous production of a mixture of substances or of a reaction mixture that has been formed by reaction of components contained therein has been found, comprising bringing together the individual components forming the mixture of substances and, in the case of the production of a reaction mixture, allowing the mixture of substances to stand in a vessel until a desired conversion has been established, said process being characterised in that the individual components are withdrawn from storage containers or from distribution networks and continuous streams of the individual components are formed. Each component stream is conveyed via a controlled system comprising a mass-flow or volume-flow measuring device and a regulating element for regulating the rate of flow. The flow-rates of the individual components are regulated in quantitatively proportional manner with reference to the flow-rate of a first component and the regulated flow-rates of the components of the mixture of substances are introduced into a receiving container, immediately or after individual flow-rates have been completely or partially conducted together.

The process according to the invention is suitable for the production of mixtures of substances consisting of at least two components but preferably consisting of more than two components. It is also possible that individual components of the mixture of substances react with one another to form secondary products, so that a reaction mixture arises. The process is accordingly especially suitable also for the production of those reaction mixtures, the reaction enthalpy of which can be managed well without additional technical effort. In this connection, the enthalpy of reaction should be capable of being dissipated substantially through the wall of the container receiving the mixture of substances, that is to say, in particular, through the wall of the transport container or storage tank.

A preferred embodiment of the process according to the invention is directed towards the production of aqueous equilibrium solutions of carboxylic acid, such as aqueous equilibrium solutions of peroxyacetic acid. In this connection a mixture of substances is formed from one or more organic carboxylic acids, water, a mineral-acid catalyst and aqueous hydrogen peroxide, from which, when allowed to stand, the equilibrium solution of peroxycarboxylic acid is formed. The chemical reaction accordingly takes place not in a special reactor or large-volume container but in the container receiving the mixture of substances. The particular advantage of the processing mode according to the invention resides, in this case and in similar cases, in the fact that a substance that is not unproblematic in terms of safety, such as a relatively highly concentrated aqueous solution of peroxycarboxylic acid, can be produced on-site at the place of demand. Hence transportation, which in certain cases is elaborate, becomes superfluous; in addition, it is possible to produce the reaction mixture in a concentration such as would preclude transportation from the point of view of safety.

With a view to producing the solutions of peroxycarboxylic acid that can be obtained in accordance with the invention, water-soluble carboxylic acids or dicarboxylic acids with 1 to 6 C atoms are preferably employed. It is possible to use pure carboxylic acids or mixtures of carboxylic acids, and mixtures of such a type may additionally also contain a water-insoluble carboxylic acid, i.e. a carboxylic acid with more than 6 C atoms.

In particularly preferred manner, solutions of peroxyacetic acid, in particular equilibrium solutions of peroxyacetic acid, are produced by the process according to the invention. In order to enhance the oxidative or disinfecting action of peroxyacetic acid it is expedient to add formic acid or a source of formic acid to the mixture of substances in addition. Suitable by way of catalyst for the establishment of equilibrium are formic acid or mineral acids such as, in particular, sulfuric acid, phosphoric acid and, particularly preferred, polyphosphoric acid.

Hydrogen peroxide is employed in varying concentration, preferably in a concentration from 30 to 85 wt. %, in particular 50 to 85 wt. %. The safety aspect is of exceptional importance in the production of peroxycarboxylic acids, since organic carboxylic acids are mixed with hydrogen peroxide of high concentration.

By virtue of the process according to the invention it is possible to adhere precisely both to the quantitative ratios of the individual components of the mixture of substances and of the reaction mixture formed therefrom and to the order of metering and hence to reliably avoid the formation of explosive mixtures.

BRIEF DESCRIPTION OF THE DRAWINGS

The process according to the invention will be further understood with reference to the accompanying drawings, wherein.

DETAILED DESCRIPTION OF THE INVENTION

Described in further detail the process of the invention is for the continuous production of a mixture of substances or of a reaction mixture that has been formed by reaction of components contained therein, comprising withdrawing the individual components from storage containers or from distribution networks, forming continuous streams of the individual components, conveying each component stream via a controlled system of mass-flow or volume-flow measuring devices and a regulating element for regulating the rate of flow, regulating the flow-rates of the individual components in quantitatively proportional manner with reference to the flow-rate of a first component and introducing the regulated flow-rates of the components of the mixture of substances into a receiving container, immediately or after individual flow-rates have been completely or partially conducted together, thereby bringing together the individual components forming the mixture of substances and, in the case of the production of a reaction mixture, allowing the mixture of substances to stand in said container until a desired conversion has been established.

Figure 1:
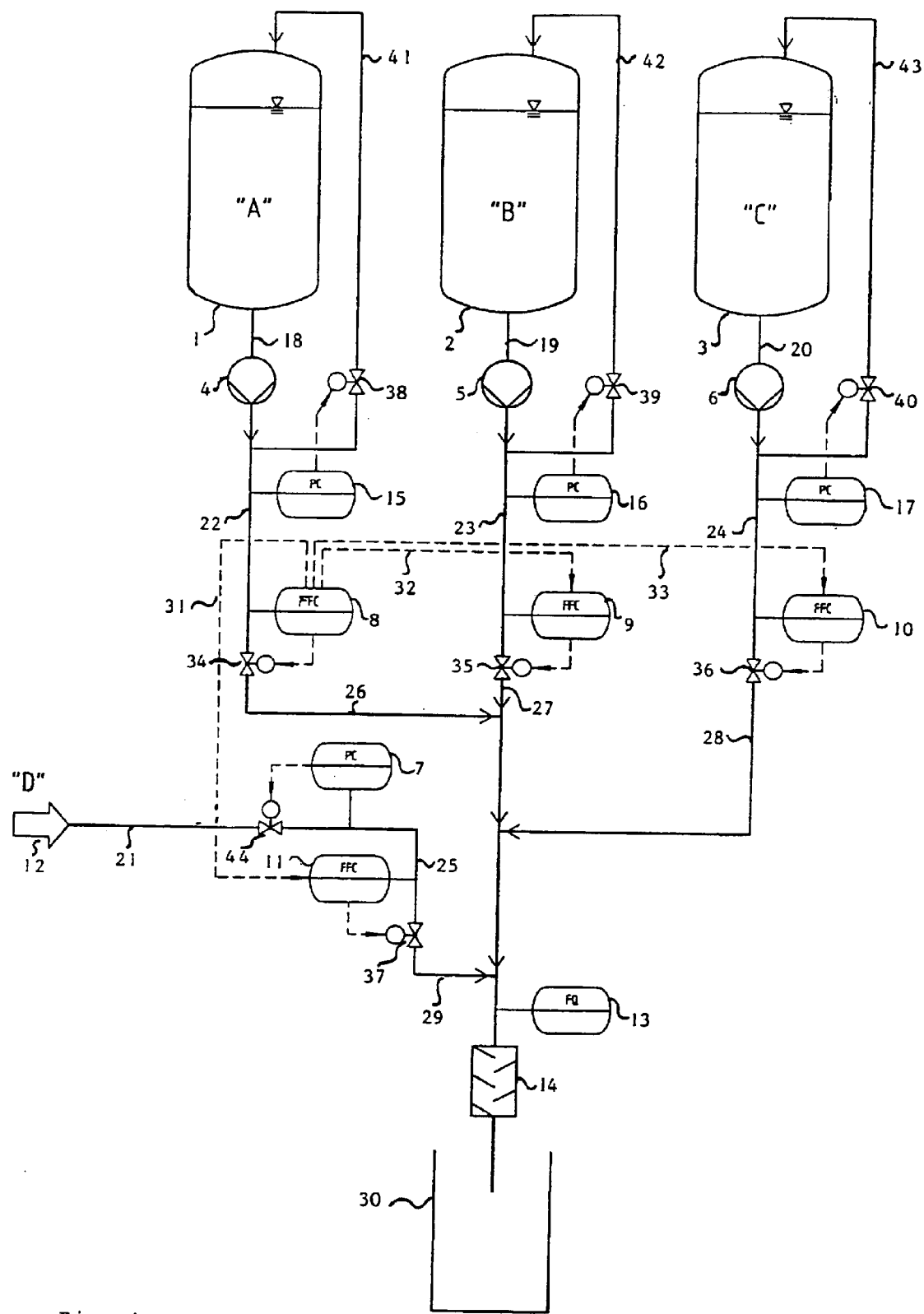
FIG. 1 is a schematic flow chart of one embodiment of the invention.
Figure 2:
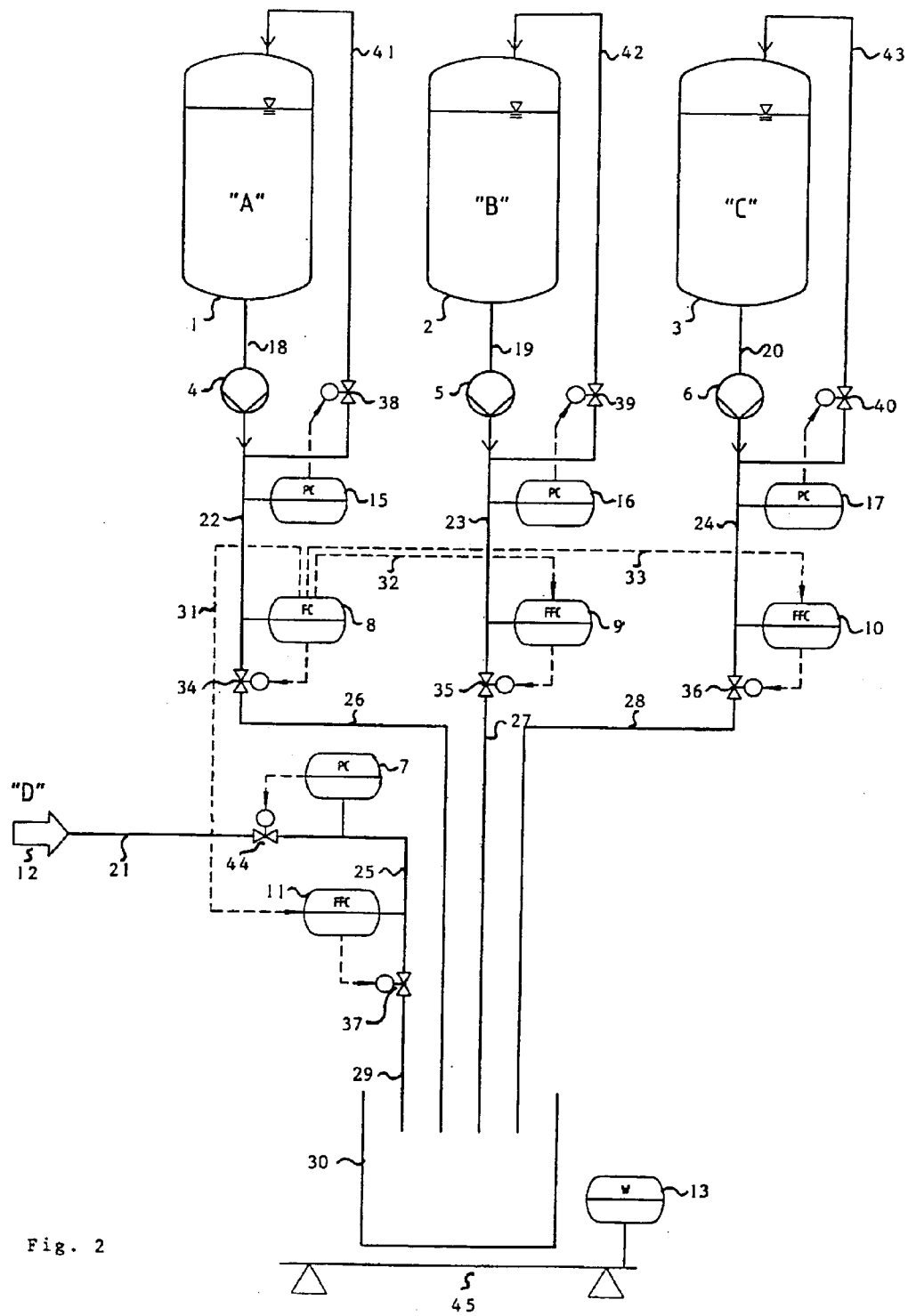
FIG. 2 is a schematic flow chart of another embodiment of the invention.

Referring now to the drawings, the individual components, such as A, B and C, of the mixture of substances to be produced are withdrawn from the storage containers 1, 2 and 3; alternatively, one or more components may also be withdrawn from distribution networks which are available at the place of production, for example component D from the distribution network 12. In this connection the individual components may be both pure substances and mixtures of substances. Even if in FIGS. 1 and 2 the substances A, B, C and D are brought into use, it is also possible to generate mixtures of substances from fewer or more components; in this case the device required for the production is adapted to the number of components.

The components that are withdrawn from the storage containers or/and from distribution networks via lines (18, 19, 20 and 21) are conveyed by means of pumps (4, 5 and 6) or by available pressure in the case of distribution networks, or by means of other means for generating an effective pressure, into a controlled system (22, 23, 24 and 25) which is present for each component. With a view to the creation of constant metering conditions, the preliminary pressure upstream of the actual controlled system can be controlled by means of known means for pressure regulation (15, 16, 17 and 7). For example, the pressure regulation in the case of the storage containers can be adjusted by means of a circulation line (41, 42 and 43) with regulating element (38, 39 and 40) located therein, whereby a control line leads from the device for the pressure regulation (15, 16 and 17) to the regulating elements (38, 39 and 40). The preliminary pressure of the component from the distribution network can be regulated and kept constant by means of the pressure regulator (7), the control line of which drives a regulating element (44).

The controlled system for each component comprises a line (22, 23, 24 and 25), a flow-measuring device (8, 9, 10 and 11) and a regulating element, in particular a regulating valve (34, 35, 36 and 37), whereby a control line emanating from the respective flow-measuring device drives the regulating element. Suitable for the flow measurement are known devices for recording the mass or the volume. In the case of volumetric flow-rate, if fluctuations in quantity are to be avoided care has to be taken to ensure constancy of temperature or to take account of the influence of the temperature on the volume. As an alternative to the combination of flow measurement and regulating valve, speed-regulated pumps or metering pumps that jointly perform the functions of the aforementioned instruments may come into operation.

The flow-rates of components A, B and C are regulated in quantitatively proportional manner with reference to a flow-rate, generally the flow-rate of the component with the greatest quantitative rate of flow (in the Figures it is a question of the flow-rate of component A). Accordingly, control lines (31, 32 and 33) pertaining to the device for the quantitative flow measurement of component A access the device for the flow measurement (9, 10 and 11) of components B, C and D. The control unit for coordinating the measurements and the regulators with one another, whereby all relevant data are stored in the system in the form of formulae, is not shown in the Figures. The control of the plant is preferably realized by means of process-management engineering. The term 'quantitatively proportional regulation' also encompasses a mechanical adjustment of a volume ratio of the individual components.

A discharge line (26, 27, 28 and 29) is connected to the controlled system of each component. According to FIG. 1 the component streams are conducted together in succession; according to FIG. 2 the flow-rates are conveyed individually into a receiving container (30). In the embodiment according to FIG. 1 the individual component streams which are regulated in quantitatively proportional manner are conducted together in succession, and the total stream reaches the receiving container (30). In order to guarantee the homogeneity in the receiving container, the united partial streams can be guided via a mixing element (14) which is preferably constructed in the form of a static mixer. From the point of view of safety engineering and quality assurance it is expedient to control the accuracy of metering by the rate of flow of the total stream after the individual component streams have been united also being measured by means of a flow-measuring device (13). From the point of view of safety, in many cases the order in which the individual component streams are conducted together is important. This order is of particular importance for the previously discussed production of solutions of peroxycarboxylic acid.

Should an adequate intermixing be guaranteed by turbulences, diffusion or by a stirrer arranged in the receiving container, the uniting of the partial streams or even the upstream connection of a mixing element can be dispensed with. In this case a quantitative control measurement can be undertaken by means of a balance (45), for example. According to a preferred embodiment, the rate of flow of the total stream that has been formed (FIG. 1) or the total quantity of the individual streams or partial streams introduced into the container or of the total stream (FIG. 2) is measured and is equalized with the sum of the individual streams.

A further subject of the invention is a system for the continuous production of mixtures of substances or of reaction mixtures for implementing the previously described process. This system comprises storage containers for the continuous production of mixtures of substances or of reaction mixtures according to the process as described herein. Included are storage containers or distribution networks for the individual components of the mixture of substances, devices for metering the individual components and a receiving container. The system features a line branching off from each storage container (1, 2, 3) or distribution network (12) which takes the form of a controlled system (22 to 25). Each controlled system exhibits a flow-measuring device (8 to 11) and a regulating element (34 to 37) for regulating the rate of flow and a regulator unit with control lines (31, 32, 33) which enables a quantitatively proportional metering of the components. The lines (26 to 29) connected downstream of the controlled systems lead into a receiving container (30), immediately or after individual lines or all lines have been conducted together. This system and also preferred embodiments thereof have already been discussed in connection with the description of the process according to the invention.

The process according to the invention and the system that has been presented herein permit, in simple and reliable manner, the production also of complex mixtures of substances and of reaction mixtures without the use of, in certain cases, elaborate reaction apparatus. By virtue of the order in which the quantitatively regulated partial streams of the individual components are conducted together, it is possible to ensure that the formation of dangerous component mixtures is avoided.

Further variations and modifications will be apparent to those skilled in the art from the foregoing and are intended to be encompassed by the claims appended hereto.

German priority application 100 48 513.8 is relied on and incorporated herein by reference.

We claim:

1. A process for the continuous production of an aqueous equilibrium peroxycarboxylic acid solution, comprising withdrawing individual components from storage containers or from distribution networks that form the equilibrium peroxycarboxylic acid solution including a lower carboxylic acid, aqueous hydrogen peroxide, water and a mineral acid catalyst, forming continuous streams of the individual components, conveying each component stream by a controlled system including a mass-flow or volume-flow measuring device and a regulating element for regulating the rate of flow, regulating mass flow-rates of the individual components in quantitatively proportional manner with reference to the mass flow-rate of a first component and introducing the regulated mass flow-rates of the individual components into a receiving container, immediately or after individual mass flow-rates have been completely or partially combined together to form a total stream, thereby bringing together the individual components forming the equilibrium peroxycarboxylic acid and, and measuring the flow of the total stream formed from the individual streams or measuring the total quantity of the individual or partial streams fed into the container and balancing total flows against the sum of the individual streams, and, allowing the mixture of substances to stand in a container until a desired conversion has been established.

2. The process according to claim 1, further comprising measuring flow by a device for mass-flow measurement or a metering pump.

3. The process according to claim 1, further comprising drawing the streams off from the storage containers and conveying them via the controlled system by pumps or by available preliminary pressure.

4. The process according to claim 2, further comprising drawing the streams off from the storage containers and conveying them via the controlled system by pumps or by available preliminary pressure.

5. The process according to claim 1, further comprising keeping regulating conditions constant by adjusting the preliminary pressure of the respective component stream upstream of the respective controlled system is adjusted to a constant value.

6. The process according to claim 2, further comprising keeping regulating conditions constant by adjusting the preliminary pressure of the respective component stream upstream of the respective controlled system is adjusted to a constant value.

7. The process according to claim 3, further comprising keeping regulating conditions constant by adjusting the preliminary pressure of the respective component stream upstream of the respective controlled system is adjusted to a constant value.

8. The process according to claim 4, further comprising keeping regulating conditions constant by adjusting the preliminary pressure of the respective component stream upstream of the respective controlled system is adjusted to a constant value.

9. The process according to claim 1, further comprising conducting quantitatively proportional component streams together in succession and homogenizing partial streams that are formed or total stream that is formed with of mixing elements.

10. The process according to claim 2, further comprising conducting quantitatively proportional component streams together in succession and homogenizing partial streams that are formed or total stream that is formed with of mixing elements.

11. The process according to claim 3, further comprising conducting quantitatively proportional component streams together in succession and homogenizing partial streams that are formed or total stream that is formed with of mixing elements.

12. The process according to claim 4, further comprising conducting quantitatively proportional component streams together in succession and homogenizing partial streams that are formed or total stream that is formed with of mixing elements.

13. The process according to claim 1, further comprising measuring rate of flow of the total stream that has formed or the total quantity of the individual streams or partial streams introduced into the container or of the total stream and equalizing with the sum of the individual streams.

14. The process according to claim 2, further comprising measuring rate of flow of the total stream that has formed or the total quantity of the individual streams or partial streams introduced into the container or of the total stream and equalizing with the sum of the individual streams.

15. The process according to claim 3, further comprising measuring rate of flow of the total stream that has formed or the total quantity of the individual streams or partial streams introduced into the container or of the total stream and equalizing with the sum of the individual streams.

16. The process according to claim 4, further comprising measuring rate of flow of the total stream that has formed or the total quantity of the individual streams or partial streams introduced into the container or of the total stream and equalizing with the sum of the individual streams.

17. The process according to claim 1, further comprising producing an aqueous equilibrium solution of peroxycarboxylic acid from the components comprising lower carboxylic acid, aqueous hydrogen peroxide, water and mineral-acid catalyst, whereby the component streams of carboxylic acid, water, mineral acid, or a partial stream containing carboxylic acid, water and mineral acid, and aqueous hydrogen peroxide are conveyed into the receiving container simultaneously in quantitatively proportional ratio or, in the case where the individual component streams have previously been conducted together, adding aqueous hydrogen peroxide by way of final component and bringing about the establishment of equilibrium by allowing the mixture to stand.

18. The process according to claim 2, further comprising producing an aqueous equilibrium solution of peroxycarboxylic acid from the components comprising lower carboxylic acid, aqueous hydrogen peroxide, water and mineral-acid catalyst, whereby the component streams of carboxylic acid, water, mineral acid, or a partial stream containing carboxylic acid, water and mineral acid, and aqueous hydrogen peroxide are conveyed into the receiving container simultaneously in quantitatively proportional ratio or, in the case where the individual component streams have previously been conducted together, adding aqueous hydrogen peroxide by way of final component and bringing about the establishment of equilibrium by allowing the mixture to stand.

19. The process according to claim 3, further comprising producing an aqueous equilibrium solution of peroxycarboxylic acid from the components comprising lower carboxylic acid, aqueous hydrogen peroxide, water and mineral-acid catalyst, whereby the component streams of carboxylic acid, water, mineral acid, or a partial stream containing carboxylic acid, water and mineral acid, and aqueous hydrogen peroxide are conveyed into the receiving container simultaneously in quantitatively proportional ratio or, in the case where the individual component streams have previously been conducted together, adding aqueous hydrogen peroxide by way of final component and bringing about the establishment of equilibrium by allowing the mixture to stand.

20. The process according to claim 4, further comprising producing an aqueous equilibrium solution of peroxycarboxylic acid from the components comprising lower carboxylic acid, aqueous hydrogen peroxide, water and mineral-acid catalyst, whereby the component streams of carboxylic acid, water, mineral acid, or a partial stream containing carboxylic acid, water and mineral acid, and aqueous hydrogen peroxide are conveyed into the receiving container simultaneously in quantitatively proportional ratio or, in the case where the individual component streams have previously been conducted together, adding aqueous hydrogen peroxide by way of final component and bringing about the establishment of equilibrium by allowing the mixture to stand.

21. The process according to claim 1, wherein the lower carboxylic acid is acetic acid.

* * * * *